(12) United States Patent
Boysen et al.

(10) Patent No.: US 10,271,860 B2
(45) Date of Patent: Apr. 30, 2019

(54) TAP GUIDE DEVICE AND SYSTEMS AND METHODS FOR USING SAME

(71) Applicant: University of Alaska Anchorage, Anchorage, AK (US)

(72) Inventors: Philip W. Boysen, Boise, ID (US); Joshua D. Gunderson, Meridian, ID (US); Anthony J. Paris, Anchorage, AK (US)

(73) Assignee: University of Alaska Anchorage, Anchorage, AK (US)

( * ) Notice: Subject to any disclaimer, the term of this patent is extended or adjusted under 35 U.S.C. 154(b) by 115 days.

(21) Appl. No.: 15/627,799

(22) Filed: Jun. 20, 2017

(65) Prior Publication Data

US 2017/0360458 A1 Dec. 21, 2017

Related U.S. Application Data

(60) Provisional application No. 62/352,331, filed on Jun. 20, 2016.

(51) Int. Cl.
| | |
|---|---|
| *B23G 1/48* | (2006.01) |
| *A61B 17/17* | (2006.01) |
| *A61B 17/88* | (2006.01) |
| *B23G 1/44* | (2006.01) |
| *A61B 17/16* | (2006.01) |
| *A61B 90/00* | (2016.01) |

(Continued)

(52) U.S. Cl.
CPC .......... *A61B 17/17* (2013.01); *A61B 17/1655* (2013.01); *A61B 17/8897* (2013.01); *B23G 1/44* (2013.01); *B23G 1/48* (2013.01); *A61B 2017/00982* (2013.01); *A61B 2017/90* (2013.01); *A61B 2017/925* (2013.01); *A61B 2090/034* (2016.02); *A61B 2090/064* (2016.02); *B23G 2240/20* (2013.01)

(58) Field of Classification Search
CPC ... B23G 1/48; B23G 1/44; B23G 1/26; B23G 1/265; B23G 1/267; B23G 2240/20; B23G 2240/32
See application file for complete search history.

(56) References Cited

U.S. PATENT DOCUMENTS

| | | | | |
|---|---|---|---|---|
| 2,286,088 A | * | 6/1942 | Harrell | B23B 23/02 408/120 |
| 3,456,534 A | * | 7/1969 | Williams | B23B 23/04 408/241 R |

(Continued)

FOREIGN PATENT DOCUMENTS

FR 1432647 A * 3/1966 ............... B23G 1/48

*Primary Examiner* — Daniel Howell
(74) *Attorney, Agent, or Firm* — Ballard Spahr LLP (57) ABSTRACT

Tap guide assembly devices, systems, and methods are disclosed herein. A tap guide assembly can have a body assembly, a tension pin assembly, a tension spring, and a setscrew. The body assembly can have an elongate body and a drill bushing. The drill bushing can have a diameter that is less than the diameter of the elongate body and can be positioned within a portion of the elongate body. The tension pin assembly can have a pin and a collar and can be configured to be received within the body assembly. The tension spring can be positioned proximate to the collar. The setscrew can be securely positioned proximate to the tension spring and within the second opening of the elongate body.

20 Claims, 5 Drawing Sheets

(51) Int. Cl.
    *A61B 17/00*       (2006.01)
    *A61B 17/90*       (2006.01)
    *A61B 17/92*       (2006.01)

(56) References Cited

U.S. PATENT DOCUMENTS

| | | | |
|---|---|---|---|
| 3,653,780 A * | 4/1972 | Ammatuna | B23G 1/48 408/241 R |
| 4,687,384 A * | 8/1987 | McCoy | B23G 1/48 408/10 |
| 4,988,243 A * | 1/1991 | Proffitt | B23G 1/48 142/53 |

* cited by examiner

TAP GUIDE DEVICE AND SYSTEMS AND METHODS FOR USING SAME

CROSS REFERENCE TO RELATED PATENT APPLICATION

This application claims priority to U.S. Provisional Application No. 62/352,331 filed Jun. 20, 2016, herein incorporated by reference in its entirety.

BACKGROUND

Tap guides have long been used in the art of drilling and tapping holes in a workpiece. When tapping or threading holes in a workpiece using conventional drilling systems, current tap guides wear, loosen, and eventually become unusable as the desired tap alignment is no longer maintained by the tap guide. Conventional tap guide designs are not serviceable and must be discarded when worn.

Thus, there is a need in the pertinent art for devices, systems, and methods that integrate wear resistant components to tap guides in order to minimize wear. There is a further need in the pertinent art for tap guides that have replaceable parts, eliminating the need to discard the entire tap guide when wear becomes excessive.

SUMMARY

Described herein, in one aspect, is a tap guide assembly. The tap guide assembly can have a body assembly, a tension pin assembly, a tension spring, and a setscrew. The body assembly can have a longitudinal axis, an elongate body, and a drill bushing. The elongate body can have a diameter, an inner surface, and outer surface, a first end, and an opposed second end. The first end of the elongate body can define a first opening and the second end of the elongate body can define a second opening. The inner surface of the elongate body can define a central bore that extends between the first opening and the second opening relative to the longitudinal axis. The drill bushing can have a bearing surface and a diameter that is less than the diameter of the elongate body. The drill bushing can be positioned at least partially within a portion of the elongate body. The tension pin assembly can be configured to be received within the body assembly. The tension pin assembly can have a pin and a collar. The pin can have a diameter, a distal end, and a proximal end. The distal end can have a sloped portion that forms a tip and extends through the first opening of the elongate body and the drill bushing relative to the longitudinal axis of the body assembly. The collar can have a diameter that is greater than the diameter of the pin. The proximal end of the pin can be securely positioned within the collar. The tension spring can be positioned proximate to the collar. The setscrew can be securely positioned proximate to the tension spring and within the second opening of the elongate body.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein:

FIG. 2A-2B is an exploded isometric view of an exemplary body assembly as disclosed herein.

FIG. 3A-3B is an exploded isometric view of an exemplary tension pin assembly as disclosed herein. FIG. 3A is an exploded isometric view of an exemplary collar as disclosed herein. FIG. 3B is an exploded isometric view of an exemplary pin as disclosed herein.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a drill bushing" can include two or more such actuators unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, the terms "threading" and "tapping" may be used interchangeably to mean the act of threading a hole.

As used herein, the terms "drill blank" and "pin" may be used interchangeably to mean the pin of the tension pin assembly.

Described herein and with reference to FIGS. 1-5, is a tap guide assembly 10. It is contemplated that the tap guide assembly 10 can be used in conjunction with a mill, a lathe, or a drill press to guide a tap into a hole. It is further contemplated, however, that the tap guide assembly 10 can be provided for use with any type of machine used for drilling or tapping holes. As is known in the art, holes are typically punched in a first operation and then threaded in a second operation. The tap guide assembly 10 disclosed herein is contemplated for use in performing the second operation. In exemplary aspects, the tap guide assembly 10 can comprise a body assembly 12, a tension pin assembly 50, a tension spring 68, and a setscrew 70, as described herein.

Figure 1:
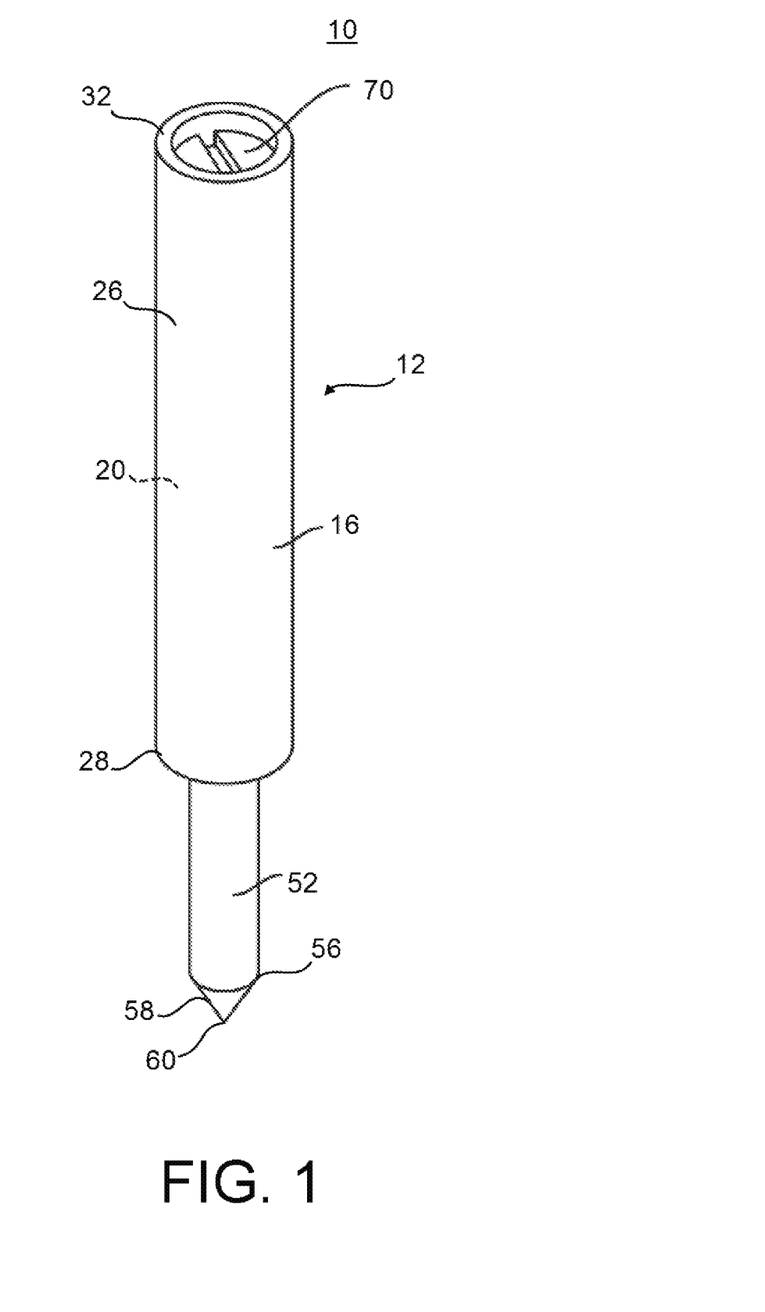
FIG. 1 is an isometric view of an exemplary tap guide assembly as disclosed herein.
Figure 2A:
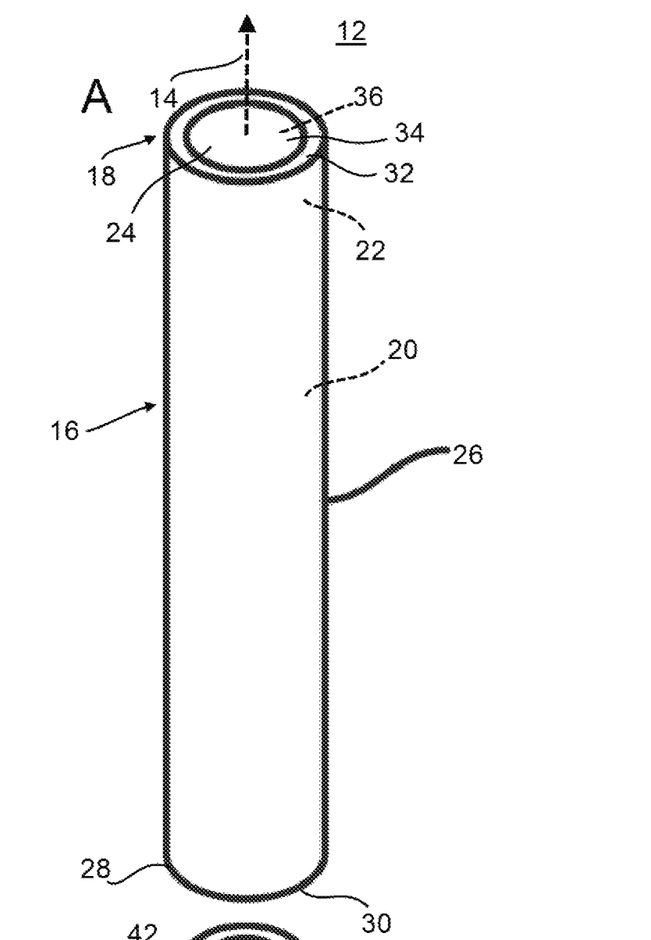
FIG. 2A is an exploded isometric view of an exemplary elongate body as disclosed herein.
Figure 2B:
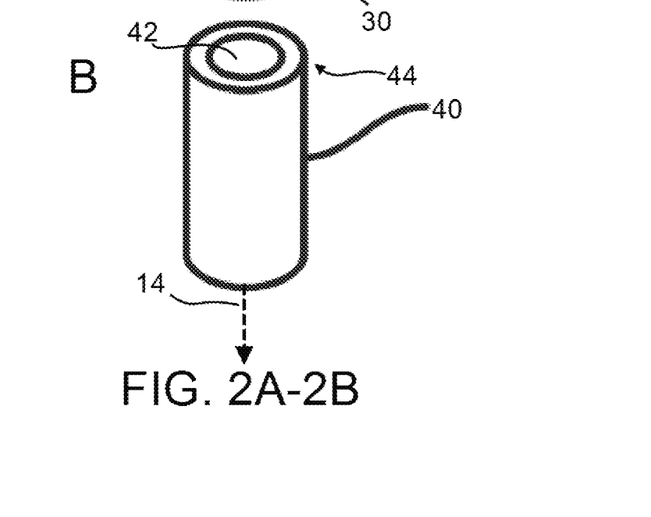
FIG. 2B is an exploded isometric view of an exemplary drill bushing as disclosed herein.
Figure 5:
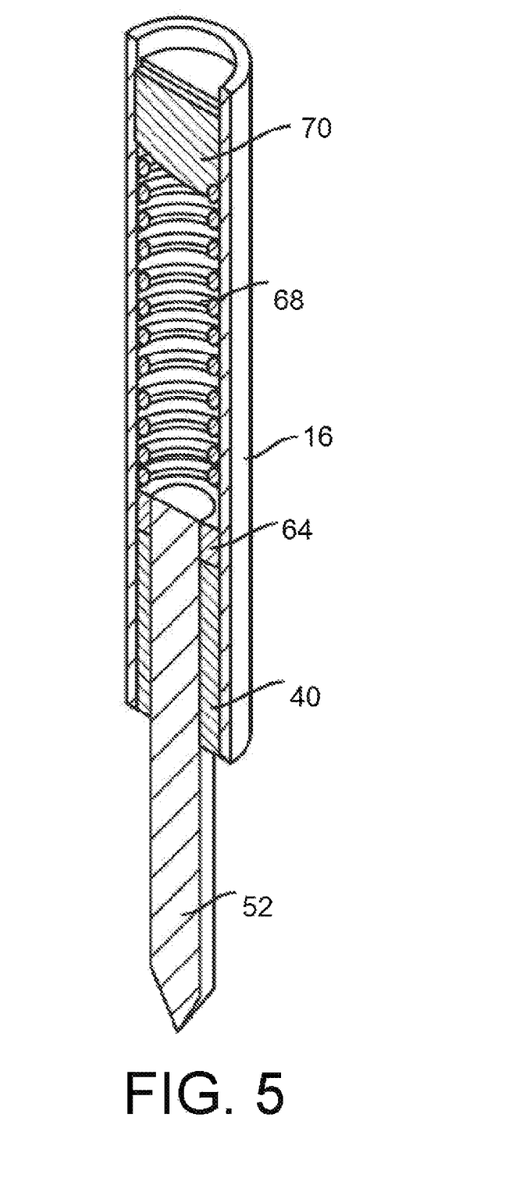
FIG. 5 is a cross-sectional view of an assembled exemplary tap guide assembly as disclosed herein.

In one aspect and with reference to FIGS. 1-2B and 5, the body assembly 12 can have a longitudinal axis 14. In this aspect, the body assembly 12 can comprise an elongate body 16 and a drill bushing 40. In a further aspect, as shown in FIG. 2A, the elongate body 16 can have a diameter 18, an inner surface 20, an outer surface 26, a first end 28, and an opposed second end 32. In this aspect, the first end 28 can define a first opening 30. In a further aspect, the second end 32 can define a second opening 34. In still a further aspect, the inner surface 20 can define a central bore 36 that extends therebetween the first opening 30 and the second opening 34 relative to the longitudinal axis 14. In these aspects, it is contemplated that at least a portion of the inner surface 20 of the elongate body 16 can comprise a threaded area 22. In another aspect, the threaded area 22 can define a receiving area 24 for the setscrew 70, as further described herein. Optionally, in an exemplary aspect, the elongate body 16 can comprise a ground steel rod, drilled and tapped for a setscrew 70 at the second end 32 of the elongate body 16. In another aspect, the elongate body 16 can comprise a ground steel rod bored for a drill bushing 40 at the first end 28. In another aspect, as shown in FIG. 2B, the drill bushing 40 can have a bearing surface 42 and a diameter 44. In another aspect, the diameter 44 of the drill bushing 40 can be less than the diameter 18 of the elongate body 16. It is contemplated that the size of the drill bushing 40 can vary depending on the size of the hole. Thus, it is further contemplated that the diameter 18 of the elongate body 16 can also vary depending on the size of the hole. In exemplary aspects, as shown in FIG. 5, the drill bushing 40 can be removably positioned at least partially within a portion of the elongate body 16. In other exemplary aspects, the drill bushing 40 can be removably positioned at least partially within the first end 28 of the elongate body 16. It is contemplated that the drill bushing 40 can be any type of drill bushing 40 that is known in the art. For example and without limitation, the drill bushing 40 can be a press-fit bushing, a renewable bushing, a liner bushing, a groove bushing, a template bushing, a coolant bushing, or combinations thereof. In a preferred aspect, however, it is contemplated that the drill bushing 40 is a press-fit bushing. In this aspect, the press-fit bushing can be any type of press-fit bushing, including, but not limited to, a head press-fit bushing and a headless press-fit bushing. In another aspect, the drill bushing 40 can be made of any material known in the art, including, but not limited to, steel, stainless steel, tungsten carbide, bronze, Oilite, brass, aluminum, iron, or combinations thereof. In a preferred aspect, the drill bushing 40 comprises steel that is heat treated to achieve a desired hardness, i.e., hardened steel.

Figures 3A, 3B:
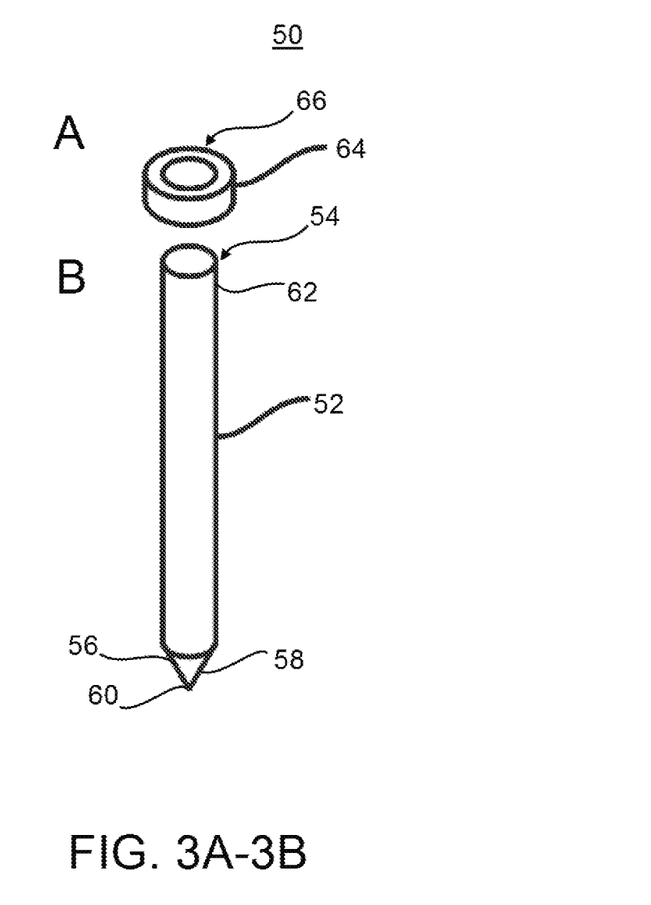

In another aspect and with reference to FIGS. 3A-3B and 5, the tension pin assembly 50 can be configured to be received within the body assembly 12. In this aspect, at least a portion of the tension pin assembly 50 can be configured for selective vertical movement relative to the longitudinal axis 14 of the body assembly 12. In one aspect, the tension pin assembly 50 can comprise a pin 52 and a collar 64. As shown in FIG. 3B, the pin 52 can have a diameter 54, a distal end 56, and a proximal end 62. In one aspect, the distal end 56 can have a sloped portion 58 that can form a tip 60. In this aspect, the tip 60 can be a rounded tip or any other shaped tip known in the art. In exemplary aspects, the distal end 56 of the pin can be symmetrically or asymmetrically sloped. It is contemplated that the pin 52 can be made from a drill blank that can be machined, in any manner known in the art, at a desired angle to create the tip 60. For example and without limitation, a drill blank can be machined to a slope ranging from about 45 degrees to about 135 degrees. Preferably, it is contemplated that drill blank can be machined to a slope ranging from about 45 degrees to about 90 degrees. More preferably, it is contemplated that the drill blank can be machined to a 60 degree slope. It is further contemplated that the machined drill blank can be of any length and diameter known in the art. Additionally, in exemplary aspects, it is contemplated that the drill blank can be made of any material known in the art, including, but not limited to, steel, stainless steel, tungsten carbide, bronze, Oilite, brass, aluminum, iron, or combinations thereof. In a preferred aspect, the drill blank comprises hardened steel.

In a further aspect, the distal end 56 of the pin 52 can be inserted into the body assembly 12 at the second opening 34 of the elongate body 16 such that the pin 52 can extend through the elongate body 16. More particularly, it is contemplated that at least a portion of the distal end 56 of the pin 52 can further extend, relative to the longitudinal axis 14 of the body assembly 12, through the drill bushing 40 and further through the first opening 30 of the elongate body 16 until at least a portion of the distal end 56 of the pin 52 protrudes outwardly from the first opening 30 of the body assembly 12 at a desired length. In these aspects, the pin 52 can be configured for selective vertical movement relative to the longitudinal axis 14 of the body assembly 12. It is contemplated that the drill bushing 40 can be configured to maintain the linear and angular alignment of the pin 52. In further aspects, the outer diameter of the pin 52 can engage the bearing surface 42 of the drill bushing 40. In these aspects, the drill bushing 40 can comprise the surface that has sliding contact with the pin 52 and thus can have a tendency to wear. To minimize such wear, components of the tap guide assembly 10 such as the drill bushing 40 and the pin 52 can comprise hardened steel, which can yield an extended life for the tap guide assembly 10.

In another aspect, the tension pin assembly 50 can have a collar 64, as shown in FIG. 3A. It is contemplated that the collar 64 can be any type of collar that is known in the art. In a preferred aspect, it is contemplated that the collar 64 is a press-fit collar. In a further aspect, the collar 64 can comprise steel. In these aspects, a press-fit steel collar rod can be stock bored for a press fit with the pin 52. In further aspects, the collar 64 can have a diameter 66 that is greater than the diameter 54 of the pin 52. In a further aspect, the proximal end 62 of the pin 52 can be securely positioned within the collar 64, as depicted in FIG. 5. It is contemplated that such secure positioning of the proximal end 62 of the pin 52 within the collar 64 can prevent further advancement of the pin 52 through the first opening 30 of the elongate body 16.

Figures 4A, 4B:
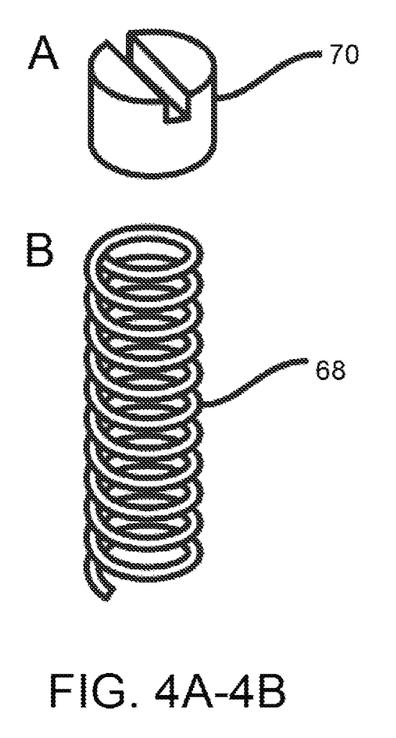
FIG. 4A is an exploded isometric view of an exemplary setscrew as disclosed herein.
FIG. 4B is an exploded isometric view of an exemplary tension spring as disclosed herein.

In another aspect and with reference to FIGS. 4A and 5, the tap guide assembly 10 can comprise a tension spring 68. It is contemplated that the tension spring 68 can be any stock spring that is known in the art. In a further aspect, the tension spring 68 can be positioned proximate to the collar 64 of the tension pin assembly 50, as illustrated in FIG. 5. In another aspect, the tension spring 68 can engage at least a portion of the diameter 66 of the collar 64. In another aspect, the tension pin assembly 50 can engage the tension spring 68 such that vertical movement of the tension pin assembly 50 effects a corresponding axial movement of the tension spring 68. In this aspect, the tension spring 68 can effect a downward vertical force on the tap as the tap advances and cuts the threads.

In another aspect and with reference to FIGS. 4B and 5, the tap guide assembly 10 can comprise a setscrew 70. It is contemplated that the setscrew 70 can be any stock setscrew 70 known in the art. In another aspect, the setscrew 70 can be securely positioned within the second opening 34 of the elongate body 16, as shown in FIG. 5. In yet another aspect, the setscrew 70 can be securely positioned proximate to the tension spring 68. In these aspects, the setscrew 70 can prevent advancement of the tension pin assembly 50 and the tension spring 68 from the second opening 34 of the elongate body 16 upon application of force to the tension pin assembly 50 and the tension spring 68 relative to the longitudinal axis 14 of the body assembly 12.

The tap guide assembly 10 disclosed herein can integrate wear resistant components known to minimize wear. In addition, the parts that have sliding contact and may become worn, such as the drill bushing 40 and the pin, are replaceable and eliminate the need of discarding the entire tap guide when wear becomes excessive. Thus, the tap guide assembly 10 disclosed herein has an extended life over conventional tap guides that are known in the art. In exemplary aspects, the body assembly 12, tension pin assembly 50, tension spring 68, and setscrew 70 form the extended-life tap guide assembly 10. In exemplary aspects, the life of the tap guide assembly 10 can be extended beyond that of existing tap guides by using the drill bushing 40 (or guide) for the bearing surface 42 in the elongate body 16 (or shank) and a drill blank for the pin 52. In these aspects, the drill bushing 40 can provide the bearing surface 42 for the pin 52. As disclosed herein, drill bushings 40 and machined drill blanks reduce production costs. In exemplary aspects, the drill bushing 40 and the drill blank, which can comprise hardened steel, minimize wear of the drill bushing 40 and the pin and are replaceable. Systems and methods for replacing the drill bushing 40 and the pin 52 are disclosed herein.

Methods and Systems for Manufacturing and/or Assembling a Tap Guide Assembly

Disclosed herein are methods and systems of manufacturing and assembling a tap guide assembly 10. Such methods comprise manufacturing a body assembly 12 that can have a longitudinal axis 14, an elongate body 16, and a drill bushing 40, as described herein. The drill bushing 40 can be inserted, at least partially, within a portion of the elongate body 16. More particularly, the drill bushing 40 can be positioned at least partially within the first end 28 of the elongate body 16. For example, if a press-fit drill bushing is used, the press-fit drill bushing can be pressed into the elongate body 16 at the first end 28 of the elongate body 16. Further, the disclosed methods and systems comprise manufacturing a tension pin assembly 50 having a pin 52 and a collar 64, as disclosed herein. The collar 64 can be rod stock bored to fit the diameter of the drill blank. To assemble the tension pin assembly 50, the proximal end 62 of the pin 52 can be securely positioned within the collar 64. If, for example and without limitation, a press-fit collar 64 is used, the collar can be pressed onto the proximal end 62 of the pin. Once assembled, the tension pin assembly 50 can be inserted into the body assembly 12 through the second opening 34 of the elongate body 16 such that the pin 52 extends through the first opening 30 of the elongate body 16 and further through the drill bushing 40 relative to the longitudinal axis 14 of the body assembly 12. The tension spring 68 can then be inserted through the second opening 34 of the elongate body 16 such that the tension spring 68 is positioned proximate to the collar 64. Once the tension spring 68 is positioned within the body assembly 12, the setscrew 70 can be positioned within the second opening 34 of the elongate body 16 and tightened such that the tension spring 68 is compressed between the tension pin assembly 50 and the setscrew 70. In exemplary aspects, the body assembly 12, tension pin assembly 50, tension spring 68, and setscrew 70 can cooperate to form the tap guide assembly 10.

Methods and Systems for Disassembling or Replacing Components of the Tap Guide Assembly Disclosed herein are methods and systems for disassembling or replacing parts of the tap guide assembly 10. To disassemble the tap guide assembly 10, the setscrew 70 can be loosened and removed from the tap guide assembly 10. Because the setscrew 70, when securely tightened within the second opening 34 of the elongate body 16, can prevent the other components of the tap guide assembly 10 that are positioned within the elongate body 16 from advancing through the second opening 34, removal of the setscrew 70 can allow the tension spring 68, the tension pin assembly 50, and the drill bushing 40 to be removed through the second opening 34. Once removed, the pin 52 and collar 64 of the tension pin assembly 50 can be disassembled by applying opposing forces to each component. Disassembly of the setscrew 70, tension spring 68, pin 52, collar 64, and drill bushing 40 from the elongate body 16 can allow for replacement of any of the described components should such replacement be necessary for reasons such as, but not limited to, excessive wear.

Methods and Systems for Threading Holes using a Tap Guide Assembly

In use, as further described herein, the tap guide assembly 10 can be used with a drilling apparatus such as a mill, lathe, or drill press to guide a tap into the hole. Usually, when a threaded hole is desired in a workpiece, a mill, a lathe, or a drill press is used. The workpiece can be placed in the mill vise, and a cutting tool can be inserted into the mill collet. The workpiece is then aligned with the cutting tool so that a hole can be cut in the workpiece. After the hole is cut, the mill collet remains aligned with the hole. The cutting tool is then removed, the tap guide assembly 10 is inserted into the mill collet, and a tap is inserted between the hole and the tap guide assembly 10. To cut the threads, the tap is turned and the threads are cut in the hole while the tap guide assembly 10 maintains an axial force on the tap and an accurate alignment of the centerline of the tap with that of the hole and prevents tap breakage.

Disclosed herein are methods and systems for threading holes using a tap guide assembly 10. In operation, a tap can be inserted between a hole in a workpiece and a tap guide assembly 10. The tap guide assembly 10 can be positioned within a spindle of a drilling machine and can comprise a body assembly 12, a tension pin assembly 50, a tension spring 68, and a setscrew 70, as described herein. A portion of the tension pin assembly 50 can be moved into an annular groove extending into an inner diameter of the tap. Once the tension pin assembly 50 is properly aligned, the tap is rotated within an inner diameter of the hole to create threads within the hole. It is contemplated that the tension spring 68 of the tap guide assembly 10 provides a downward vertical force on the tension pin assembly 50.

Exemplary Aspects

In view of the described tap guide assembly 10 devices, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A tap guide assembly, comprising: a body assembly having a longitudinal axis, comprising: an elongate body having a diameter, an inner surface, an outer surface, a first end, and an opposed second end, the first end defining a first opening, the second end defining a second opening, and the inner surface defining a central bore extending therebetween the first opening and the second opening relative to the longitudinal axis, a drill bushing having a bearing surface and a diameter that is less than the diameter of the elongate body and removably positioned at least partially within a portion of the elongate body; a tension pin assembly configured to be received within the body assembly and comprising: a pin having a diameter, a distal end and a proximal end, the distal end having a sloped portion that forms a tip and extending therethrough the first opening of the elongate body and the drill bushing relative to the longitudinal axis of the body assembly such that at least a portion of the distal end of the pin protrudes outwardly from the body assembly, a collar having a diameter greater than the diameter of the pin, the proximal end of the pin being securely positioned within the collar; a tension spring positioned proximate to the collar; and a setscrew securely positioned within the second opening of the elongate body and proximate to the tension spring.

Aspect 2: The tap guide assembly of aspect 1, wherein at least a portion of the inner surface of the elongate body comprises a threaded area.

Aspect 3: The tap guide assembly of any one of the preceding aspects, wherein the threaded area defines a receiving area for the setscrew.

Aspect 4: The tap guide assembly of any one of the preceding aspects, wherein the drill bushing is selected from the group consisting of: a press-fit bushing, a renewable bushing, a liner bushing, a groove bushing, a template bushing, a coolant bushing, and combinations thereof.

Aspect 5: The tap guide assembly of any one of the preceding aspects, wherein the drill bushing is a press-fit bushing.

Aspect 6: The tap guide assembly of any one of the preceding aspects, wherein the press-fit bushing is selected from the group consisting of: a head press-fit bushing and a headless press-fit bushing.

Aspect 7: The tap guide assembly of any one of the preceding aspects, wherein the drill bushing comprises a material selected from the group consisting of steel, stainless steel, tungsten carbide, titanium nitride, bronze, Oilite, brass, aluminum, iron, and combinations thereof.

Aspect 8: The tap guide assembly of any one of the preceding aspects, wherein the drill bushing is configured to maintain the linear and angular alignment of the pin.

Aspect 9: The tap guide assembly of any one of the preceding aspects, wherein the outer diameter of the pin can engage the bearing surface of the drill bushing.

Aspect 10: The tap guide assembly of any one of the preceding aspects, wherein the distal end of the pin is symmetrically sloped.

Aspect 11: The tap guide assembly of any one of the preceding aspects, wherein the slope is in the range of 45 to 90 degrees.

Aspect 12: The tap guide assembly of any one of the preceding aspects, wherein the tip of the pin is rounded.

Aspect 13: The tap guide assembly of any one of the preceding aspects, wherein the slope is in the range of 45 to 90 degrees.

Aspect 14: The tap guide assembly of any one of the preceding aspects, wherein the pin is configured for selective vertical movement relative to the longitudinal axis of the body assembly.

Aspect 15: The tap guide assembly of any one of the preceding aspects, wherein the collar engages at least a portion of the diameter of the collar.

Aspect 16: The tap guide assembly of any one of the preceding aspects, wherein the collar is a press-fit collar.

Aspect 17: The tap guide assembly of any one of the preceding aspects, wherein the collar prevents further advancement of the pin from the body assembly.

Aspect 18: The tap guide assembly of any one of the preceding aspects, wherein the tension spring engages at least a portion of the diameter of the collar.

Aspect 19: The tap guide assembly of any one of the preceding aspects, wherein the setscrew prevents advancement of the tension pin assembly and the tension spring from the second opening of the elongate body upon application of force to the tension pin assembly and the tension spring relative to the longitudinal axis of the body assembly.

Aspect 20: A method of manufacturing a tap guide assembly, comprising: manufacturing a body assembly having a longitudinal axis, comprising: an elongate body having a diameter, an inner surface, an outer surface, a first end, and an opposed second end, the first end defining a first opening, the second end defining a second opening, and the inner surface defining a central bore extending therebetween the first opening and the second opening relative to the longitudinal axis, a drill bushing having a diameter that is less than the diameter of the elongate body; inserting the drill bushing at least partially within a portion of the elongate body; manufacturing a tension pin assembly configured to be received within the body assembly and comprising: a pin having a diameter, a distal end and a proximal end, the distal end having a sloped portion that forms a tip, a collar having a diameter greater than the diameter of the pin; securely positioning the proximal end of the pin within the collar; inserting the tension pin assembly through the second opening of the elongate body such that the pin extends through the first opening of the elongate body and the drill bushing relative to the longitudinal axis of the body assembly; inserting the tension spring through the second opening of the elongate body such that the tension spring is positioned proximate to the collar; and tightening a setscrew within the second opening of the elongate body such that the tension spring is compressed between the tension pin assembly and the setscrew, wherein the body assembly, the tension pin assembly, the tension spring, and the setscrew cooperate to form the tap guide assembly.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A tap guide assembly, comprising:
    a body assembly having a longitudinal axis, comprising:
        an elongate body having a diameter, an inner surface, an outer surface, a first end, and an opposed second end, the first end defining a first opening, the second end defining a second opening, and the inner surface defining a central bore extending therebetween the first opening and the second opening relative to the longitudinal axis,
        a drill bushing having a bearing surface and a diameter that is less than the diameter of the elongate body and removably positioned at least partially within a portion of the elongate body;
    a tension pin assembly configured to be received within the body assembly and comprising:
        a pin having a diameter, a distal end and a proximal end, the distal end having a sloped portion that forms a tip and extending therethrough the first opening of the elongate body and the drill bushing relative to the longitudinal axis of the body assembly such that at least a portion of the distal end of the pin protrudes outwardly from the body assembly,
        a collar having a diameter greater than the diameter of the pin, the proximal end of the pin being securely positioned within the collar;
    a tension spring positioned proximate to the collar; and
    a setscrew securely positioned within the second opening of the elongate body and proximate to the tension spring.

2. The tap guide assembly of claim 1, wherein at least a portion of the inner surface of the elongate body comprises a threaded area.

3. The tap guide assembly of claim 2, wherein the threaded area defines a receiving area for the setscrew.

4. The tap guide assembly of claim 1, wherein the drill bushing is selected from the group consisting of: a press-fit bushing, a renewable bushing, a liner bushing, a groove bushing, a template bushing, a coolant bushing, and combinations thereof.

5. The tap guide assembly of claim 1, wherein the drill bushing is a press-fit bushing.

6. The tap guide assembly of claim 5, wherein the press-fit bushing is selected from the group consisting of: a head press-fit bushing and a headless press-fit bushing.

7. The tap guide assembly of claim 1, wherein the drill bushing comprises a material selected from the group consisting of steel, stainless steel, tungsten carbide, titanium nitride, bronze, Oilite, brass, aluminum, iron, and combinations thereof.

8. The tap guide assembly of claim 1, wherein the drill bushing is configured to maintain the linear and angular alignment of the pin.

9. The tap guide assembly of claim 1, wherein the outer diameter of the pin can engage the bearing surface of the drill bushing.

10. The tap guide assembly of claim 1, wherein the distal end of the pin is symmetrically sloped.

11. The tap guide assembly of claim 10, wherein the slope is in the range of 45 to 90 degrees.

12. The tap guide assembly of claim 11, wherein the tip of the pin is rounded.

13. The tap guide assembly of claim 1, wherein the slope is in the range of 45 to 90 degrees.

14. The tap guide assembly of claim 1, wherein the pin is configured for selective vertical movement relative to the longitudinal axis of the body assembly.

15. The tap guide assembly of claim 1, wherein the collar engages at least a portion of the diameter of the collar.

16. The tap guide assembly of claim 1, wherein the collar is a press-fit collar.

17. The tap guide assembly of claim 1, wherein the collar prevents further advancement of the pin from the body assembly.

18. The tap guide assembly of claim 1, wherein the tension spring engages at least a portion of the diameter of the collar.

19. The tap guide assembly of claim 1, wherein the setscrew prevents advancement of the tension pin assembly and the tension spring from the second opening of the elongate body upon application of force to the tension pin assembly and the tension spring relative to the longitudinal axis of the body assembly.

20. A method of manufacturing a tap guide assembly, comprising:
    manufacturing a body assembly having a longitudinal axis, comprising:
        an elongate body having a diameter, an inner surface, an outer surface, a first end, and an opposed second end, the first end defining a first opening, the second end defining a second opening, and the inner surface defining a central bore extending therebetween the first opening and the second opening relative to the longitudinal axis,
        a drill bushing having a diameter that is less than the diameter of the elongate body;
    inserting the drill bushing at least partially within a portion of the elongate body;
    manufacturing a tension pin assembly configured to be received within the body assembly and comprising:
        a pin having a diameter, a distal end and a proximal end, the distal end having a sloped portion that forms a tip,
        a collar having a diameter greater than the diameter of the pin;
        securely positioning the proximal end of the pin within the collar;
    inserting the tension pin assembly through the second opening of the elongate body such that the pin extends through the first opening of the elongate body and the drill bushing relative to the longitudinal axis of the body assembly;

inserting the tension spring through the second opening of the elongate body such that the tension spring is positioned proximate to the collar; and tightening a setscrew within the second opening of the elongate body such that the tension spring is compressed between the tension pin assembly and the setscrew, wherein the body assembly, the tension pin assembly, the tension spring, and the setscrew cooperate to form the tap guide assembly.

* * * * *